(12) United States Patent
Ross et al.

(10) Patent No.: US 10,214,487 B2
(45) Date of Patent: Feb. 26, 2019

(54) INDOLE DERIVATIVES AND METHODS OF USING THE SAME

(75) Inventors: David Ross, Boulder, CO (US); Philip Reigan, Northumberland (GB); David Siegel, Denver, CO (US); Christopher J. Moody, Leicestershire (GB); Marie A. Colucci, Nottingham (GB); Donna Dehn, Castle Rock, CO (US)

(73) Assignee: The Regents of the Univeresity of Colorado, a body corporate, Denver, CO (US)

( * ) Notice: Subject to any disclaimer, the term of this patent is extended or adjusted under 35 U.S.C. 154(b) by 956 days.

(21) Appl. No.: 11/908,395

(22) PCT Filed: Feb. 27, 2006

(86) PCT No.: PCT/US2006/007340
§ 371 (c)(1),
(2), (4) Date: Sep. 9, 2008

(87) PCT Pub. No.: WO2006/098884
PCT Pub. Date: Sep. 21, 2006

(65) Prior Publication Data
US 2009/0227652 A1    Sep. 10, 2009

Related U.S. Application Data

(60) Provisional application No. 60/660,913, filed on Mar. 11, 2005.

(51) Int. Cl.
*C07D 209/12*  (2006.01)
*A61K 31/404*  (2006.01)

(52) U.S. Cl.
CPC .................... *C07D 209/12* (2013.01)

(58) Field of Classification Search
CPC ............................ C07D 209/12; A61K 31/404
USPC .......................................... 548/485; 514/418
See application file for complete search history.

(56) References Cited

U.S. PATENT DOCUMENTS 3,206,471 A * 9/1965 Allen, Jr. .............. C07C 205/37
548/469
3,265,698 A * 8/1966 Allen, Jr. .............. C07C 205/37
544/143
6,156,744 A    12/2000 Ross et al.

FOREIGN PATENT DOCUMENTS

WO    WO 97/23456    7/1997

OTHER PUBLICATIONS

Allen et al., Journal of the American Chemical Society (1964), 86(18), 3877-8.*
Allen et al., Journal of Medicinal Chemistry (1966), 10(1), 14-22.*
Mercado et al, Antimicrobial Agents an dChemotherapy (1972), 1(1), 73-7.*
Winski et al., Biochemistry, vol. 40, No. 50, 2001, pp. 15135-15142.*
Naylor et al., J. Med. Chem, 1998, 41, 2720-2731.*

(Continued)

*Primary Examiner* — Rebecca L Anderson
(74) *Attorney, Agent, or Firm* — Sheridan Ross P.C.

(57) ABSTRACT

The invention provides indole-4,7-dione derivatives useful for the treatment of diseases in a mammal, pharmaceutical compositions containing the same and methods of using the same in the treatment of cancer and neoplastic diseases including human solid tumors and other mammalian tumors.

7 Claims, 2 Drawing Sheets

(56) References Cited

OTHER PUBLICATIONS

Beall, et al., "Indolequinone antitumor agents: correlation between quinone structure, rate of metabolism by recombinant human NQ01 and in vitro cytotoxicity", Journal of Medicinal Chemistry, 1998, vol. 41, pp. 4755-4766.
Cotterill, et al., "Cyclopropamitosenes, Novel Bioreductive Anticancer Agents. Synthesis, Electrochemistry, and Biological Activity of 7-Substituted Cyclopropamitosenes and Related Indolequinones", Journal Medicinal Chemistry, 1994, vol. 37, pp. 3834-3843.
Cullen, et al., "Dicumarol inhibition of NADPH:quinine oxidoreductase induces growth inhibition of pancreatic cancer via a superoxide-mediated mechanism", Cancer Research, 2003, vol. 63, pp. 5513-5520.
Dehn, et al., "Biochemical, cytotoxic, and genotoxic effects of ES936, a mechanism-based inhibitor of NAD(P)H:quinine oxidoreductase 1, in cellular systems", Molecular Pharmacology, 2003, vol. 64, No. 3, pp. 714-720.
Everett, et al., "Controlling the rates of reductively activated elimination from the (indol-3-yl) methyl position of indolequinones", J. Chem. Soc., Perkin Trans., 2001, vol. 2, pp. 843-860.
Hammons, et al., "Increased DT-diaphorase activity in transformed and tumorigenic pancreatic acinar cells", Cancer Letters, 1995, vol. 96, pp. 9-14.
Iyengar, et al., "New 2-Substituted Indologuinone Mitomycin Analogues", Journal of Medicinal Chemistry, American Chemical Society, Jan. 1, 1989, vol. 32, No. 8, pp. 1866-1872.
Iyengar, et al., "Nucleotide derivatives on 2,7-diaminomitosene", Journal of Medicinal Chemistry, 1988, vol. 31, pp. 1579-1585.
Jaffar, et al., "3-Substituted-5-azirindinyl-1-methylindole-4,7-diones as NQ01-directed antitumour agents: mechanism of activation and cytotoxicity in vitro", Biochemical Pharmacology, 2003, vol. 66, pp. 1199-1206.
Logsdon, et al., "Molecular profiling of pancreatic adenocarcinoma and chronic pancreatitis identifies multiple genes differentially regulated in pancreatic cancer", Cancer Research, May 15, 2003, vol. 63, pp. 2649-2657.
Maliepaard, et al., "Role of lipophilicity in the in vitro antitumor activity of a series of new mitosene compounds", Anti-Cancer Drug Design, 1992, vol. 7, No. 5, pp. 415-425.
Moody, et al., "Novel bioreductive, anticancer agents based on indolequinones", IL Farmaco, 1997, vol. 52, pp. 271-279.
Naylor, et al., "Indolequinone anti-tumor agents: reductive activation and elimination from (5-methoxy-1,2-dimethyl-4, 7-dioxo-indol-3-yl)methyl derivatives and hypoxia-selectivecytotoxicity in vitro", J. Med. Chem., 1998, vol. 41, pp. 2720-2731.
Siegel, et al., "NAD(P)H: Quinone oxidoreductase 1: Role as a superoxide scavenger", Molecular Pharmacology, 2004, vol. 65, No. 5, pp. 1238-1247.
Skibo, et al, "Aziridinyl Quinone Antitumor Agents Based on Indoles and Cyclopent[b]indoles: Structure-Activity Relationships for Cytotoxicity and Antitumor Activity", Journal of Medicinal Chemistry, 2001, vol. 44, No. 22, pp. 3545-3562.
Swann, et al., "Indolequinone antitumor agents: Correlation between Quinone Structure and Rate of Metabolism by Recombinant Human NAD(P)H: Quinone Oxidoreductase Part 2", Journal of Medicinal Chemistry, 2001, vol. 44, No. 20, pp. 3311-3319.
Swann, et al., Rates of reductive-elimination of substituted nitrophenols from the (indo 1-3-yl) methyl position of indolequinones, J. Chem. Soc., Perkin Trans., 2001, vol. 2, pp. 1340-1345.
Cotterill, et al., "Cyclopropamitosenes, Novel Bioreductive Anticancer Agents. Synthesis of 7-Methoxycyclopropamitosene and Related Indolequinones", Tetrahedron, 1994, vol. 50, No. 25, pp. 7657-7674.
Verboom, et al, "Novel bioreductive mitosene and nitosane analogs of mitomycin C", Anti-Cancer Drug Design, 1987, vol. 2, No. 3, pp. 271-277.
Winski, et al., "Characterization of a Mechanism-Based Inhibitor of NAD(P)H:Quinone Oxidoreductase 1 by Biochemical, X-ray Crystallographic, and Mass Spectrometric Approaches", Biochemistry, 2001, vol. 40, pp. 15135-15142.
Extended European Search Report for EP Patent Application No. 06736627.8, dated Jun. 16, 2009.
International Search Report for International (PCT) Application No. PCT/US06/07340, dated Jun. 28, 2006.
Written Opinion for International (PCT) Application No. PCT/US06/07340, dated Jun. 28, 2006.
International Preliminary Report on Patentability for International (PCT) Application No. PCT/US06/07340, dated Sep. 12, 2007.

* cited by examiner

INDOLE DERIVATIVES AND METHODS OF USING THE SAME

GOVERNMENT INTEREST

This invention was made with Government support under CA51210 awarded by the National Institutes of Health (NIH). The Government has certain rights in the invention.

FIELD OF THE INVENTION

The invention relates to indole-4,7-dione derivatives, pharmaceutical compositions containing the same, and methods of using these compounds in the treatment of diseases.

BACKGROUND OF THE INVENTION

NAD(P)H:quinone oxidoreductase 1 (NQO1; EC 1.6.99.2; originally called DT-diaphorase), is a highly inducible, obligate two-electron reductase present in a wide variety of mammalian tissues. The enzyme can detoxify both natural and synthetic xenobiotics and, when expressed in high levels, can scavenge intracellular superoxide.

NQO1 has been exploited in cancer therapy as a bioactivating enzyme for various antitumor quinones. Using this approach, cancer cells expressing high levels of NQO1 accumulate greater levels of these activated antitumor quinones, which in turn kill the cell. Recently however, the contradictory approach of inhibiting NQO1 has been shown to lead to the inhibition of cell growth and to cell death following the increased production and accumulation of intracellular superoxide. This presents a new treatment modality for mammalian tumors expressing NQO1 wherein inhibition of NQO1 leads to cell death through intracellular superoxide accumulation.

Studies showing the accumulation of superoxide following NQO1 inhibition were conducted with the NQO1 inhibitor, dicumarol. Dicumarol is the only commercially-available inhibitor of NQO1. Unfortunately, dicumarol is a non-specific, competitive inhibitor known to have many ancillary effects, including the inhibition of many dehydrogenase and reductase enzymes such as glutathione-S-transferase and glutathione peroxidase, UDP-glucuronosyltransferase, and a variety of stress-activated protein kinases, particularly at high doses. Dicumarol has also been reported to inhibit mitochondrial oxidative phosphorylation and NFkB activation. Thus, there has been a search for compounds that specifically inhibit NQO1.

SUMMARY OF THE INVENTION

The invention relates to indole-4,7-dione derivatives that have been identified in a search for compounds that specifically inhibit NQO1 and methods of using these compounds to treat disease states in an mammal. Specifically, the invention provides methods of using these compounds to kill or inhibit the growth of cancer cells.

One embodiment of the invention is a compound of Formula (I):

Formula I or a pharmaceutically acceptable salt thereof, wherein:

$R^1$ and $R^2$ are independently H, $C_{1-6}$ alkyl, $C_{3-8}$ cycloalkyl, $C_{2-4}$ alkenyl, $C_{2-4}$ alkynyl, $C_{1-4}$ alkoxy, or $C_{1-6}$ alkyl optionally substituted with hydroxy, mercapto, halide, $C_{1-6}$ alkyl, $C_{1-6}$ alkenyl, $C_{1-4}$ alkoxy, $OR^7$, $SR^7$, $NR^7R^8$, $CO_2R^7$, $OC(\!=\!O)R^9$, heteroaryl, or any combination thereof, or aryl or heteroaryl optionally substituted with hydroxy, mercapto, nitro, halide, $C_{1-6}$ alkyl, $C_{1-6}$ alkenyl, $C_{1-4}$ alkoxy, $OR^7$, $SR^7$, $NR^7R^8$, $CO_2R^7$, or any combination thereof, or

$R^1$ and $R^2$ together form a heterocyclic ring, of 5-8 members, including the indole nitrogen, optionally substituted with hydroxy, mercapto, halide, $C_{1-6}$ alkyl, $C_{2-4}$ alkenyl, $C_{1-4}$ alkoxy, aryl, heteroaryl, $NR^7R^8$, $OR^7$, $SR^7$, $CO_2R^7$, $OC(\!=\!O)R^9$, or any combination thereof;

$R^3$ is H, $C_{1-6}$ alkyl, $C_{3-8}$ cycloalkyl, $C_{2-4}$ alkenyl, $C_{2-4}$ alkynyl, $C_{1-4}$ alkoxy or aryl.

$R^4$ is $OR^{10}$ wherein $R^{10}$ is H, $C_{1-6}$ alkyl, $C_{3-8}$ cycloalkyl, $C_{2-4}$ alkenyl, $C_{2-4}$ alkynyl, $C(\!=\!O)R^9$, aryl or heteroaryl optionally substituted with hydroxy, mercapto, amino, nitro, carboxylic acid, sulfonic acid, halide, trihalomethyl, $C_{1-6}$ alkyl, $C_{1-6}$ alkenyl, $C_{1-4}$ alkoxy, $OR^7$, $SR^7$, $NR^7R^8$, $CO_2R^7$, $C(\!=\!O)R^9$, or any combination thereof;

$R^5$ and $R^6$ are independently H or $C_{1-6}$ alkyl, $C_{3-8}$ cycloalkyl, $C_{2-4}$ alkenyl, $C_{2-4}$ alkynyl, $C_{1-4}$ alkoxy, aryl, heteroaryl, $OR^7$, $SR^7$, $NR^7R^8$, $CO_2R^7$, $OC(\!=\!O)R^9$, or $C_{1-6}$ alkyl optionally substituted with hydroxy, mercapto, amino, sulfonic acid, carboxylic acid, halide $C_{1-6}$ alkyl, $C_{1-6}$ alkenyl, $C_{1-4}$ alkoxy, $OR^7$, $SR^7$, $NR^7R^8$, $CO_2R^7$, $OC(\!=\!O)R^9$, heteroaryl, or any combination thereof, wherein when $R^1$ and $R^2$ are $CH_3$, $R^3$ is H, and $R^4$ is hydroxymethyl, acetyloxy, (aminocarbonyl)oxy, phenoxy or para-nitrophenoxy, $R^5$ cannot be methoxy and wherein when $R^1$ and $R^2$ are $CH_3$, $R^3$ is H, and $R^4$ is hydroxymethyl, $R^6$ cannot be methoxy;

or, $R^5$ and $R^6$ together form a heterocyclic ring having the chemical formula:

$R^7$ and $R^8$ are independently H, $C_{1-6}$ alkyl, $C_{3-8}$ cycloalkyl, $C_{2-4}$ alkenyl, aryl, heteroaryl, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(\!=\!O)R^9$, heteroaryl, or any combination thereof, or $R^7$ and $R^8$ together form a heterocyclic ring optionally substituted with hydroxy, mercapto, halide, $C_{1-6}$ alkyl;

$R^9$ is H, $C_{1-6}$ alkyl, $C_{3-8}$ cycloalkyl, $C_{2-4}$ alkenyl, $C_{2-4}$ alkynyl, heteroaryl, aryl or $NR^7R^8$; and, $R^{11}$ and $R^{12}$ are independently H, $C_{1-6}$ alkyl, or $C_{3-8}$ cycloalkyl.

One embodiment of the invention is a compound of Formula (I) or pharmaceutically acceptable salts thereof wherein:

$R^1$ and $R^2$ are independently H, $C_{1-6}$ alkyl, $C_{3-8}$ cycloalkyl, or $C_{1-6}$ alkyl optionally substituted with hydroxy, mercapto, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or any combination thereof;

$R^3$ is H or $C_{1-6}$ alkyl;

$R^4$ is $-OR^{10}$ wherein $R^{10}$ is alkyl, $C(=O)R^9$, wherein $R^9$ is H, $-CH_3$, $-NH_2$, or $-CH_2CH_3$, heteroaryl or aryl optionally substituted with hydroxy, mercapto, amino, nitro, carboxylic acid, sulfonic acid, halide, trihalomethyl, $C_{1-6}$ alkyl, $C_{1-6}$ alkenyl, $C_{1-4}$ alkoxy, $OR^7$, $SR^7$, $NR^7R^8$, $CO_2R^7$, $C(=O)R^9$, or any combination thereof;

$R^5$ and $R^6$ are independently H, $OR^7$, $SR^7$, $NR^7R^8$ or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or any combination thereof, wherein when $R^1$ and $R^2$ are $CH_3$, $R^3$ is H, and $R^4$ is hydroxymethyl, acetyloxy, (aminocarbonyl)oxy, phenoxy or para-nitrophenoxy, $R^5$ cannot be methoxy and wherein when $R^1$ and $R^2$ are $CH_3$, $R^3$ is H, and $R^4$ is hydroxymethyl, $R^6$ cannot be methoxy; and, $R^7$ and $R^8$ are independently H, $C_{1-6}$ alkyl, $C_{3-8}$ cycloalkyl, $C_{2-4}$ alkenyl, aryl, heteroaryl, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$. $OC(=O)R^9$, heteroaryl, or any combination thereof, or $R^7$ and $R^8$ together form a heterocyclic ring optionally substituted with hydroxy, mercapto, halide, or $C_{1-6}$ alkyl.

Another embodiment of the present invention is a compound of Formula (I) or pharmaceutically acceptable salts or pro-drug forms thereof wherein:

$R^1$ and $R^2$ are independently H, $C_{1-6}$ alkyl, $C_{3-8}$ cycloalkyl, or $C_{1-6}$ alkyl optionally substituted with hydroxy, mercapto, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or any combination thereof;

$R^3$ is H;

$R^4$ is $-OR^{10}$ wherein $R^{10}$ is nitrophenyl or $C(=O)R^9$, wherein $R^9$ is $-CH_3$, or $-NH_2$;

$R^5$ and $R^6$ are independently H, $OR^7$, $SR^7$, $NR^7R^8$, $CO_2R^7$, $OC(=O)R^9$, heteroaryl, or any combination thereof, wherein when $R^1$ and $R^2$ are $CH_3$, and $R^4$ is hydroxymethyl, acetyloxy, (aminocarbonyl)oxy, phenoxy or para-nitrophenoxy, $R^5$ cannot be methoxy and wherein when $R^1$ and $R^2$ are $CH_3$, and $R^4$ is hydroxymethyl, $R^6$ cannot be methoxy; and, $R^7$ and $R^8$ are independently H, $C_{1-6}$ alkyl, $C_{3-8}$ cycloalkyl, $C_{2-4}$ alkenyl, aryl, heteroaryl, or $R^7$ and $R^8$ together form a heterocyclic ring optionally substituted with hydroxy, mercapto, halide, or $C_{1-6}$ alkyl.

Preferred embodiments of this invention are compounds of Formula (I), or pharmaceutically acceptable salts thereof, wherein:

$R^1$ is H or $C_{1-3}$ alkyl;
$R^2$ is H or $C_{1-3}$ alkyl;
$R^3$ is H;
$R^4$ is $-OR^{10}$ wherein $R^{10}$ is nitrophenyl or $C(=O)R^9$, wherein $R^9$ is $-CH_3$ or $-NH_2$;

$R^5$ and $R^6$ are independently H or $OCH_3$, wherein when $R^1$ and $R^2$ are $CH_3$ and $R^4$ is acetyloxy, (aminocarbonyl)oxy, or para-nitrophenoxy, $R^5$ cannot be methoxy.

Particularly preferred embodiments of the invention include compounds selected from:

6-methoxy-1,2-dimethyl 3-[(4-nitrophenoxy)methyl]-indole-4,7-dione, 6-methoxy-1,2-dimethyl-3-[(acetyloxy)methyl]-indole-4,7-dione, 6-methoxy-1,2-dimethyl-3-[(aminocarbonyloxy)methyl]-indole-4,7-dione, and 5-methoxy-2-hydroxymethyl-1-methyl-3-[(4-nitrophenoxy)methyl]-indole-4,7-dione, and pharmaceutically acceptable salts and pro-drug forms thereof.

Related embodiments of the present invention include methods of treating a disease in a mammal by contacting the mammal with at least one compound of the present invention. The methods of the invention may also include contacting cancer cells that have been cultured in vitro or in vivo, such as in cell culture or in an animal, with a compound of the present invention to kill or inhibit the growth of the cancer cells. Similarly, these methods include the administration of a therapeutically effective amount of at least one of the compounds of the invention to a mammal in need of such treatment. These methods of administration can include the administration of therapeutically effective amounts of pharmaceutically-acceptable salts, or solvates, or metabolites or prodrug forms of the compounds of Formula I to a mammal to treat a disease state in the mammal such as a cancer.

The invention also encompasses pharmaceutical compositions containing at least one of the compounds of Formula I and a pharmaceutically-acceptable carrier or excipient and methods of killing or inhibiting the growth of a cancer cell by contacting the cell with at least one of these pharmaceutical compositions. The compounds present in these pharmaceutical compositions may be in the form of pharmaceutically-acceptable salts, or solvates, or metabolites or prodrug forms of the compounds of Formula I described above.

DETAILED DESCRIPTION OF THE INVENTION

The present invention provides novel methods of treating a disease in a mammal by administering a therapeutically effective amount of one of the compounds of Formula I to the mammal. These methods may include killing or inhibiting the growth of cancer cells in the mammal. While not intending to be bound by any one theory, the mechanisms by which the compounds of Formula I inhibit or kill cancer cells is understood to include inhibition of NADPH:Quinone oxidoreductase 1 (NQO1). The compounds that modulate NQO1 enzymatic activity are mechanism-based "suicide" inhibitors of NQO1. This mechanism is in direct contrast to non-specific inhibitors like dicumarol that are reversible, competitive inhibitors of NQO1, and many other enzymes. It is believed that an irreversible inhibitor of NQO1 will function to elevate intracellular levels of superoxide radicals in neoplastic cells through the inhibition of NQO1 that would otherwise scavenge intracellular superoxide. The elevated levels of superoxide resulting from this enzyme inhibition may result in reduced growth and inhibition of the malignant phenotype of the cell and ultimately, death of the cell. Cancer cells having high NQO1 enzymatic activity are particularly susceptible to this mechanism of retarding cell growth or inducing cellular death by the accumulation of superoxide radicals following NQO1 inhibition. Cancers known to have high NQO1 enzymatic activity include lung, liver, kidney, colon and pancreas tumor tissues.

Many reductases are capable of catalyzing the one-electron reduction of quinones to semiquinone radicals and, under aerobic conditions, subsequent interaction of semiquinones with molecular oxygen can occur to produce superoxide. This process is termed "redox cycling" since it continues until pyridine nucleotide cofactors for the one electron reductases are exhausted or the system goes anaerobic. Similarly, redox cycling is also possible when a quinone is reduced via two-electron reductases, such as NQO1, to generate an oxygen-unstable hydroquinone. This process may be particularly relevant in cancer cells expressing high levels of NQO1. The two-electron reduction of quinones such as streptonigrin and β-lapachone has been shown to lead to redox cycling and the production of superoxide.

Cells contacted with NQO1 inhibitors do not undergo NQO1-mediated redox cycling. It is believed that redox cycling may be avoided in cells contacted with certain indole-4,7-dione derivatives due to the rapid loss of a leaving group at the 3-position of the indole ring of these compounds and subsequent interaction of the reactive iminium species in the active site of the NQO1 enzyme. This enables the use of such compounds for the treatment of cancer cells by the inhibition of NQO1 without generating oxidative stress via redox cycling reactions.

Thus, these methods encompass the treatment of diseases, including cancers in mammals, by administering to a mammal in need of such treatment an inhibitor of NQO1. Preferably, the inhibitor of NQO1 is a specific inhibitor that predominately affects the enzymatic activity of NQO1 without substantially affecting the activity of other enzymes.

The NQO1 inhibiting compounds of some embodiments of this invention may have one or more asymmetric centers or planes and it will be appreciated by those skilled in the art that compounds of the invention having a chiral center may exist in, and be isolated in, optically active and racemic forms. Additionally, some compounds may exhibit polymorphism. It is to be understood that the present invention encompasses any chiral (enantiomeric and diastereomeric) racemic, optically-active, polymorphic, or stereoisomeric forms, or mixtures thereof, of the compounds of the present invention. Many geometric isomers of olefins, C=N double bonds, and the like can also be present in these compounds, and all such stable isomers are also contemplated in the present invention. It is well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-cancer and anti-tumor activity using the in vitro and in vivo tests described herein, or using other similar tests which are well known in the art. In each instance, all chiral, (enantiomeric and diastereomeric) and racemic forms and all geometric isomeric forms or a structure are intended, unless the specific stereochemistry or isomer form is specifically indicated in this disclosure.

The term "alkyl" as used herein is directed to a saturated hydrocarbon group (designated by the formula $C_nH_{2n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., Hawley's Condensed Chemical Dictionary (13 ed.), R. J. Lewis, ed., J. Wiley & Sons, Inc., New York (1997)). Aryl groups include, without limitation, phenyl, naphthyl and quinone.

"Heteroaryl" rings are aryl rings in which one or more, typically from 1-4, of the ring-member carbon atoms is/are replaced by an atom other than a carbon atom, i.e., a heteroatom (typically O, N or S). Heteroaryl includes, without limitation: morpholinyl, piperazinyl, piperidinyl, pyridyl, pyrrolidinyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, indolinyl, indolyl-4,7-dione, 1,2-dialkyl-indolyl, 1,2-dimethyl-indolyl, and 1,2-dialkyl-indolyl-4,7-dione.

"Alkoxy" means —OR where R is alkyl as defined above, e.g., methoxy, ethoxy, propoxy, 2-propoxy and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched divalent hydrocarbon radical of three to six carbon atoms, containing at least one triple bond, e.g., ethynyl, propynyl, and the like.

Substituent groupings, e.g., $C_{1-6}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen atoms on the designated atom is/are replaced with a selection from the indicated group, provided that the designated atom's normal valency is not exceeded, and that the substitution results in a stable compound.

"Unsubstituted" atoms bear all of the hydrogen atoms dictated by their valency. When a substituent is "keto," then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

"Pharmaceutically-acceptable salts" refer to derivatives of the disclosed compounds in which the parent compound is modified by making acid or base salts thereof. Examples of pharmaceutically-acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically-acceptable salts are those forms of compounds, suitable for use in contact with the tissues of human beings and animals without causing excessive toxicity, irritation, allergic response, or other problems or complication, commensurate with a reasonable benefit/risk ratio.

Pharmaceutically-acceptable salt forms of compounds provided herein are synthesized from the parent compound which contains a basic or acidic moiety by conventional chemical methods. Generally, such salts are prepared, for example, by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is incorporated herein by this reference.

"Prodrugs" are considered to be any covalently bonded carriers which release the active parent drug of Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples or prodrugs include, but are not limited to, acetate, formate and benzoate derivatives of alcohol and amine functional groups in the compounds of Formula (I), and the like. Compounds that function effectively as prodrugs of the compounds of Formula I may be identified using routine techniques known in the art. For examples of such prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8, 1-38 (1992); d) H. Bundgaard, et al., Journal of Pharmaceutical Sciences, 77:285 (1988); and e) N. Kakeya, et al., Chem. Pharm. Bull., 32: 692 (1984), each of which is specifically incorporated herein by reference.

In addition, the invention also includes solvates, metabolites, and pharmaceutically acceptable salts of compounds of Formulas I.

The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of compounds of Formulas I, including compounds produced by a process comprising contacting a compound of this invention with a mammal for a period of time sufficient to yield a metabolic product thereof.

The term "specific inhibitor" as used herein means an inhibitor that inhibits one protein more than another protein. For example, a potential inhibitor of NQO1 is considered to be specific for NQO1 over another reductase protein when there is, preferably, at least 10- to 100-fold or greater, and most preferably about 1000-fold difference in inhibition of NQO1 compared to the other reductase.

The term "therapeutically effective amount" of a compound of this invention means an amount effective to prevent, treat, kill, reduce the growth or inhibit the malignant phenotype of neoplastic cells in a mammalian host.

The compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described in Cotterill, A. S. et al., *Cyclopropamitosenes, novel bioreductive anticancer agents. Synthesis of 7-methoxycyclopropa-mitosene and related indolequinones*. Tetrahedron, 50:7657-74 (1994); Cotterill, A. S. et al., *Cyclopropamitosenes, novel bioreductive anticancer agents. Synthesis, electrochemistry and biological activity of 7-substituted cyclopropamitosenes and related* indolequinones, J. Med. Chem., 37:3834-43 (1994); Moody, C. J. and Swann, E., *Novel bioreductive anticancer agents based on indolequinones*, Farmaco 52:271-279 (1997); Naylor, M. A. et al., *Indolequinone anti-tumor agents: reductive activation and elimination from (5-methoxy-1,2-dimethyl-4,7-dioxo-indol-3-yl)methyl derivatives and hypoxia-selective cytotoxicity* in vitro, J. Med. Chem., 41: 2720-31 (1998); Beall, H. D. et al., *Indolequinone antitumor agents: correlation between quinone structure, rate of metabolism by recombinant human NQO1 and in vitro cytotoxicity*, J. Med. Chem., 41:4755-66 (1998); Everett, S. A., et al., *Controlling the rates of reductively activated elimination from the (indol-3-yl)methyl position of indolequinones*, J. Chem. Soc., Perkin Trans. 2:843-60 (2001); Swami, E., et al., *Rates of reductive elimination of substituted nitrophenols from the (indol-3-yl)methyl position of indolequinones*, J. Chem. Soc., Perkin Trans. 2:1340-45 (2001); Swann, E., et al., *Indolequinone antitumor agents: correlation between quinone structure and rate of metabolism by recombinant human NAD(P)H: quinone oxidoreductase. Part* 2, J. Med. Chem. 44, 3311-19 (2001). These references, providing detailed synthetic methodology, are incorporated herein, in their entirety, by this reference.

Figure 1:
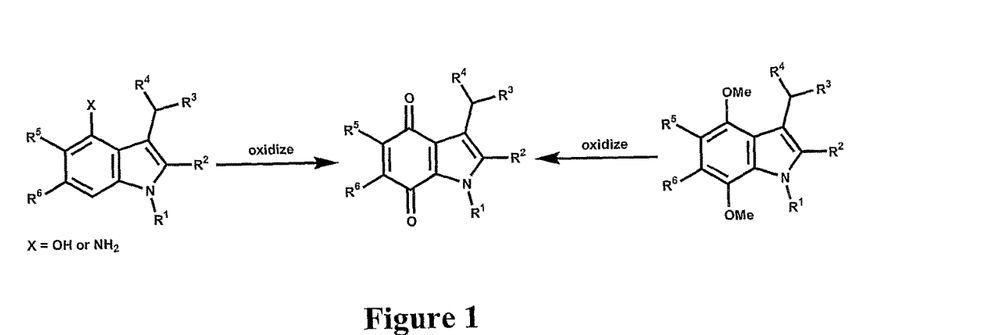
FIGS. 1 to 3 show synthetic schemes used in the methods of making the compounds of the present invention.
Figure 2:
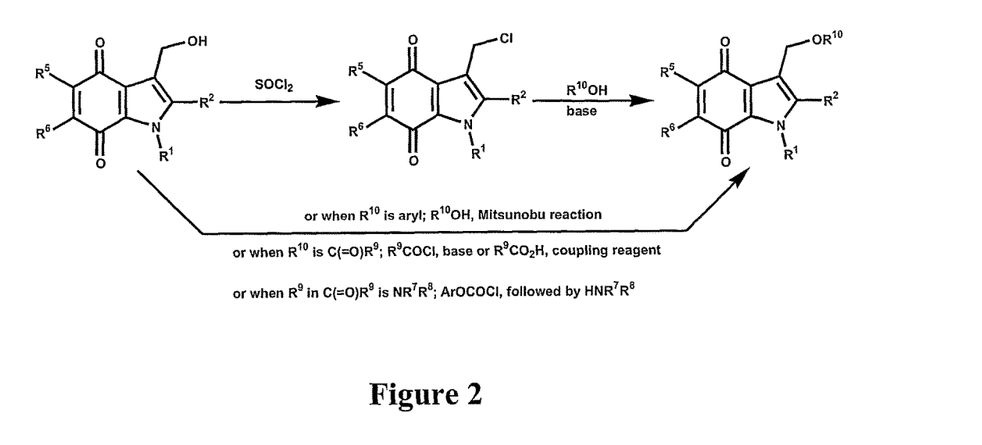
Figure 3:
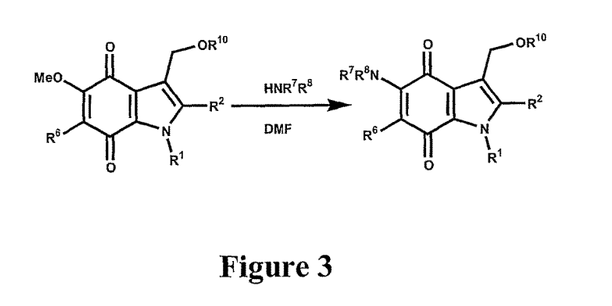

The compounds of this invention may be prepared using the reactions and techniques described in these references and shown more specifically for the compounds of the present invention in the synthetic schemes of FIGS. 1-3. The reactions are performed in solvents appropriate to the reagents and materials employed and suitable for the transformation being effected. Also, in the description of the synthetic methods described below, it is to be understood that all proposed reaction conditions, including the choice of solvents, reaction temperature, duration of the experiments and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions on the use of substituents that are compatible with the reaction conditions will be readily apparent to one skilled in the art and alternate methods must then be used.

Compounds of Formula I are prepared by the methods outlined in the synthetic schemes shown in FIGS. 1 to 3 with reference to the definitions of the substitutents to Formula I provided above. Referring to the reaction scheme shown in FIG. 1, starting indolequinones are typically made by oxidation of the corresponding 4-hydroxy- or 4-amino-indoles using oxidants such as potassium nitrosodisulfonate (Fremy's salt) or air/oxygen in the presence of salcomine. Alternatively, 4,7-dimethoxyindoles are oxidized to the corresponding quinones using cerium(IV) ammonium nitrate.

Referring to the synthetic scheme shown in FIG. 2, an appropriately-substituted indolequinone is then converted into a chloride that is further reacted with a nucleophile, such as an alcohol or phenol, in the presence of a base. Alternatively, phenols can be coupled to the indolequinone alcohol (2) using the Mitsunobu reactions, or the alcohols (2) can be directly acylated with acids ($R^9CO_2H$) under standard conditions. Carbamates can be made from the indolequinone alcohols by reaction with an aryl chloroformate followed by reaction with the amine $HNR^7R^8$. In some cases, when $R^5$ or $R^6$ are methoxy groups, they are readily displaced by other nucleophilic moieties such as alkoxides, or amines as exemplified in the reaction scheme shown in FIG. 3.

Also provided herein are pharmaceutical compositions comprising compounds of this invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted.

The compounds of the invention are effective in treating diseases over a wide dosage range and are generally administered in a therapeutically-effective amount. The dosage and manner of administration will be defined by the application of the compound and can be determined by routine methods of clinical testing to find the optimum dose. These doses are expected to be in the range of 0.001 mg/kg to 100 mg/kg of active compound. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

When employed as pharmaceuticals, the compounds of Formula I are administered in the form of pharmaceutical compositions. These compounds can be administered by a variety of routes including oral, rectal, transdermal, subcutaneous, intravenous, intramuscular, and intranasal. Preferably, the anti-cancer compounds of the present invention are administered via intratracheal instillation or aerosol inhalation when used to treat lung cancer. Such pharmaceutical compositions are prepared in a manner well known in the pharmaceutical art and comprise at least one active anti-cancer compound of Formula I.

The pharmaceutical compositions of the present invention contain, as the active ingredient, one or more of the compounds described by Formula I above, associated with pharmaceutically acceptable formulations. In making the compositions of this invention, the active ingredient is usually mixed with an excipient, diluted by an excipient or enclosed within a carrier, which can be in the form of a capsule, sachet, paper or other container. An excipient is usually an inert substance that forms a vehicle for a drug. When the excipient serves as a diluent, it can be a solid, semi-solid, or liquid material, which acts as a vehicle, carrier or medium for the active ingredient. Thus, the compositions can be in the form of solutions, syrups, aerosols (as a solid or in a liquid medium), ointments containing, for example, up to about 30% by weight of the active compound, soft and hard gelatin capsules, suppositories, sterile injectable solutions, and sterile packaged powders.

In preparing a formulation, it may be necessary to mill the anti-cancer compound to provide the appropriate particle size prior to combining with the other ingredients. If the anti-cancer compound is substantially insoluble, it ordinarily is milled to a particle size of less than 200 mesh. If the anti-cancer compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, gum Arabic, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, about 0.1 mg to about 500 mg of the active ingredient of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectal or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the MISTOMETER™ (Wintrop) and MEDIHALER™ (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

This invention further provides a method of treating a subject afflicted with a neoplasm or neoplastic disorder, by administering to the subject a pharmaceutical composition containing one or more of the compounds of Formula I described above. Such compositions generally comprise a therapeutically effective amount of a compound provided herein, that is, an amount effective to ameliorate, lessen, inhibit the growth of, or destroy, neoplastic tissue. Such amounts typically comprise from about 0.1 to about 1000 mg of the compound per kilogram of body weight of the subject to which the composition is administered. Therapeutically effective amounts can be administered according to any dosing regimen satisfactory to those of ordinary skill in the art.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention.

What is claimed is:

1. A compound having the structure:

Formula I or a pharmaceutically acceptable salt thereof, wherein:

$R^1$ and $R^2$ are independently $C_{1-6}$ alkyl optionally substituted with hydroxy, $C_{1-6}$ alkyl, $C_{1-6}$ alkenyl, $C_{1-4}$ alkoxy, $OR^7$, $NR^7R^8$, or a combination thereof, $R^3$ is H, or $C_{1-6}$ alkyl $R^4$ is $OR^{10}$ wherein $R^{10}$ is aryl or heteroaryl optionally substituted with hydroxy, mercapto, amino, carboxylic acid, sulfonic acid, trihalomethyl, $C_{1-6}$ alkyl, $C_{1-6}$ alkenyl, $C_{1-4}$ alkoxy, $SR^7$, $NR^7R^8$, $CO_2R^7$, $C(=O)R^9$, or any combination thereof;

$R^5$ is $C_{1-6}$ alkyl, $C_{3-8}$ cycloalkyl, $C_{2-4}$ alkenyl, $C_{2-4}$ alkynyl, aryl, heteroaryl, $NR^7R^8$, $CO_2R^7$, $OC(=O)R^9$, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or a combination thereof, $R^6$ is H or $C_{1-6}$ alkyl, $C_{3-8}$ cycloalkyl, $C_{2-4}$ alkenyl, $C_{2-4}$ alkynyl, $C_{1-4}$ alkoxy, aryl, heteroaryl, $OR^7$, $SR^7$, $NR^7R^8$, $CO_2R^7$, $OC(=O)R^9$, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or a combination thereof;

$R^7$ and $R^8$ are independently H, $C_{1-6}$ alkyl, $C_{3-8}$ cycloalkyl, $C_{2-4}$ alkenyl, aryl, heteroaryl, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or a combination thereof, or $R^7$ and $R^8$ together form a heterocyclic ring optionally substituted with hydroxy, mercapto, halide, $C_{1-6}$ alkyl; and $R^9$ is H, $C_{1-6}$ alkyl, $C_{3-8}$ cycloalkyl, $C_{2-4}$ alkenyl, $C_{2-4}$ alkynyl, heteroaryl, aryl or $NR^7R^8$.

2. The compound of claim 1, wherein:
$R^1$ and $R^2$ are independently $C_{1-6}$ alkyl optionally substituted with hydroxy, $C_{1-6}$ alkyl, $C_{1-6}$ alkenyl, $C_{1-4}$ alkoxy, $OR^7$, $NR^7R^8$, or a combination thereof;
$R^3$ is H or $C_{1-6}$ alkyl;
$R^4$ is $-OR^{10}$ wherein $R^{10}$ is aryl optionally substituted with hydroxy, mercapto, amino, carboxylic acid, $C_{1-6}$ alkyl, $C_{1-6}$ alkenyl, $C_{1-4}$ alkoxy, $SR^7$, $NR^7R^8$, $CO_2R^7$, $C(=O)R^9$, or a combination thereof;
$R^5$ is $C_{1-6}$ alkyl optionally substituted with hydroxy, amino, sulfonic acid, carboxylic acid, halide, $C_{1-6}$ alkyl, $C_{1-6}$ alkenyl, $C_{1-4}$ alkoxy, $NR^7R^8$, $CO_2R^7$, heteroaryl, or any combination thereof;
$R^6$ is H, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or any combination thereof; and,
$R^7$ and $R^8$ are independently H, $C_{1-6}$ alkyl, $C_{3-8}$ cycloalkyl, $C_{2-4}$ alkenyl, aryl, heteroaryl, or $C_{1-6}$ alkyl optionally substituted with hydroxy, amino, carboxylic acid, halide, $C_{1-6}$ alkyl, $C_{1-6}$ alkenyl, $C_{1-4}$ alkoxy, $OR^7$, $NR^7R^8$, $CO_2R^7$, $OC(=O)R^9$, heteroaryl, or a combination thereof, or $R^7$ and $R^8$ together form a heterocyclic ring optionally substituted with hydroxy, mercapto, halide, or $C_{1-6}$ alkyl.

3. A pharmaceutical composition comprising a compound of claim 1 and a pharmaceutically-acceptable carrier.

4. A compound having the structure:

Formula I or a pharmaceutically acceptable salt thereof, wherein:
$R^1$ is H, or
$C_{1-6}$ alkyl optionally substituted with hydroxy, $NR^7R^8$, or a combination thereof,
$R^2$ is
$C_{1-6}$ alkyl substituted with hydroxy,
$C_{1-4}$ alkoxy, $OR^7$, $NR^7R^8$, or a combination thereof,
$R^3$ is H, or $C_{1-6}$ alkyl,

$R^4$ is $OR^{10}$ wherein $R^{10}$ is aryl or heteroaryl optionally substituted with hydroxy, mercapto, amino, nitro, carboxylic acid, sulfonic acid, halide, trihalomethyl, $C_{1-6}$ alkyl, $C_{1-6}$ alkenyl, $C_{1-4}$ alkoxy, $OR^7$, $SR^7$, $NR^7R^8$, $CO_2R^7$, $C(=O)R^9$, or any combination thereof;

$R^5$ and $R^6$ are independently H or $C_{1-4}$ alkoxy, $OR^7$, $SR^7$, $NR^7R^8$,

$R^7$ and $R^8$ are independently H, $C_{3-8}$ cycloalkyl, $C_{2-4}$ alkenyl, aryl, heteroaryl, or $C_{1-6}$ alkyl optionally substituted with hydroxy, mercapto, amino, sulfonic acid, carboxylic acid, halide, $C_{1-6}$ alkyl, $C_{1-6}$ alkenyl, $C_{1-4}$ alkoxy, $OR^7$, $SR^7$, $NR^7R^8$, $CO_2R^7$, $OC(=O)R^9$, heteroaryl, or a combination thereof; and, $R^9$ is H, $C_{1-6}$ alkyl, $C_{3-8}$ cycloalkyl, $C_{2-4}$ alkenyl, $C_{2-4}$ alkynyl, heteroaryl, aryl or $NR^7R^8$.

5. A compound of claim 4, having the structure:

6. A compound having the structure:

or a pharmaceutically acceptable salt thereof.

7. A compound having the structure:

or a pharmaceutically acceptable salt thereof.

* * * * *